United States Patent [19]
Skewis

[11] Patent Number: 5,652,955
[45] Date of Patent: Aug. 5, 1997

[54] WRIST PROTECTOR

[76] Inventor: Kathleen A. Skewis, 2701 N. Ocean Blvd., #307, Boca Raton, Fla. 33431

[21] Appl. No.: 620,352

[22] Filed: Mar. 22, 1996

[51] Int. Cl.$^6$ ............................................. A41D 13/00
[52] U.S. Cl. .............................. 2/20; 2/16; 602/21
[58] Field of Search ............................... 2/16, 20, 162, 2/2; 602/21

[56] References Cited

U.S. PATENT DOCUMENTS

| | | | |
|---|---|---|---|
| 315,512 | 4/1885 | Kearns | 602/21 |
| 633,220 | 9/1899 | Sholl | 2/20 |
| 1,377,103 | 5/1921 | Suhr | 2/16 |
| 3,423,095 | 1/1969 | Cox | 2/16 |
| 3,908,197 | 9/1975 | Griffin | 2/20 |
| 4,138,108 | 2/1979 | Robinson | 273/54 B |
| 4,881,533 | 11/1989 | Teurlings | 128/87 R |
| 5,295,948 | 3/1994 | Gray | 602/21 |
| 5,339,465 | 8/1994 | Kyewski | 2/20 |
| 5,537,692 | 7/1996 | Dorr | 2/16 |

OTHER PUBLICATIONS

Inline Mar. 1995 pp. 49–52.

*Primary Examiner*—Bibhu Moranty
*Attorney, Agent, or Firm*—Alvin S. Blum

[57] ABSTRACT

A hand and wrist protector for skaters has two rigid formed plates which are securely strapped to the wrist with wide hook and loop straps. A first plate extends from the wrist down to a palm portion with a concave inner surface and a hard abrasion resistant outer surface. A second plate extends from the wrist down to a dorsal hand portion with a convex inner surface which prevents hyperextension of the wrist joint. The inner surfaces are covered with a resilient moisture absorbing surface. The palm portion and dorsal hand portions are free of attachment at their anterior and lateral edges so that the thumb and fingers are unrestrained and perspiration is more readily evaporated.

13 Claims, 1 Drawing Sheet

U.S. Patent
Aug. 5, 1997
5,652,955
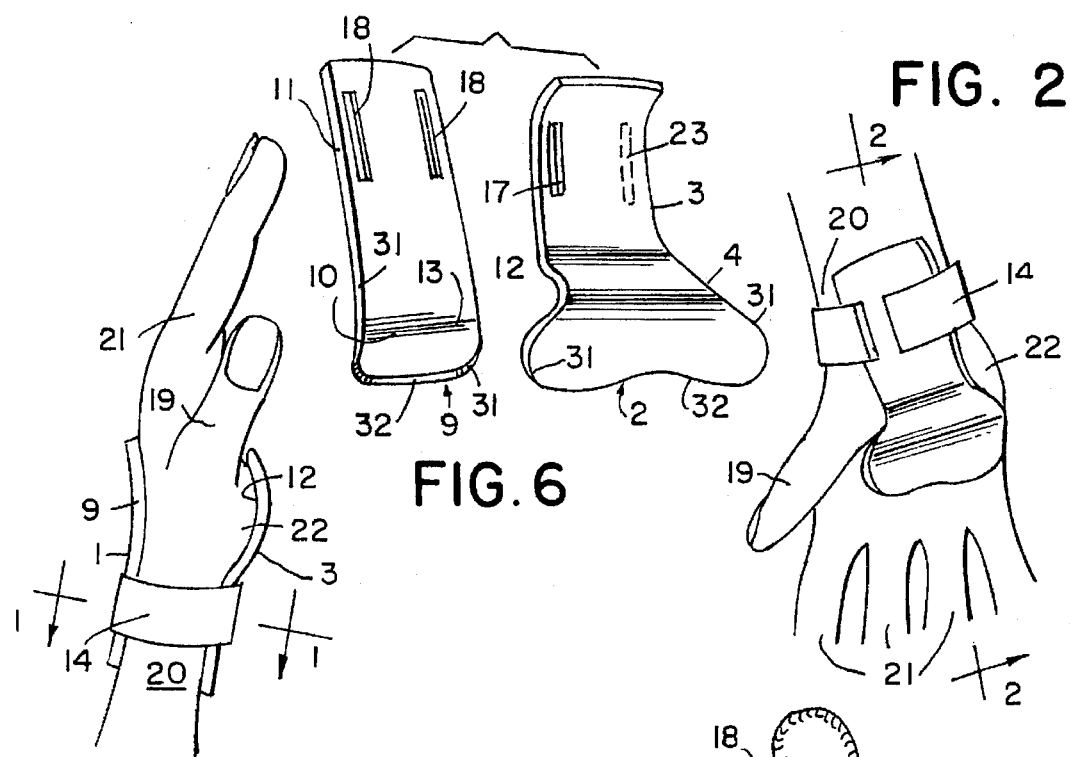
FIG. 2
FIG. 6
FIG. 1
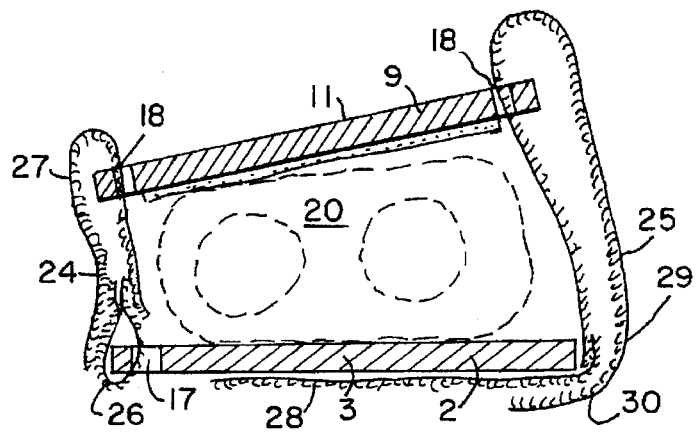
FIG. 3
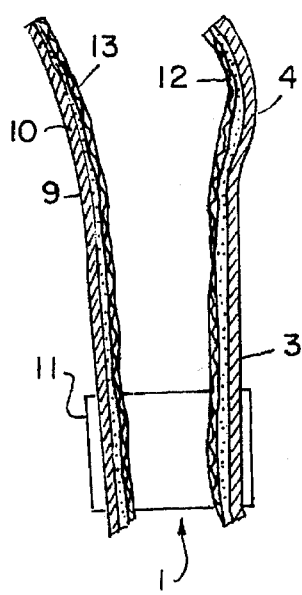
FIG. 4
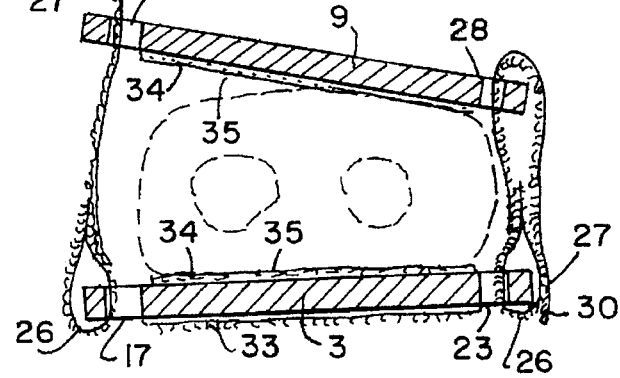
FIG. 5

WRIST PROTECTOR

FIELD OF THE INVENTION

This invention relates to wrist braces and more particularly to wrist protectors to be worn by skaters to protect the hand and wrist from injury in a fall.

BACKGROUND OF THE INVENTION

With the development of in-line skates, skaters are moving faster and traveling over surfaces that are not as uniform as in the past. This has resulted in many serious injuries from falls. Effective helmets, elbow and knee pads are now available. In a forward fall, it is instinctive to move the hands forward to break the fall. This often results in serious injury to wrist from hyperextension of the joint as well as trauma to the hand. Hand and wrist protective gloves for various sports such as bowling are well known. With the recent popularity of in-line skating and the injuries resulting therefrom, many vendors are now providing hand wrist protective gloves for that sport as well.

These gloves generally encircle and enclose the hand, leaving the ends of the fingers and thumb free. They extend down the wrist and provide some rigid reinforcement between palm and wrist. They are confining, making use of the hands very awkward such as in putting on the second glove. They enclose so much of the hand that the vigorous skater will soak the gloves through with perspiration within a short time. Many skaters discard the gloves, preferring the potential danger of injury to the immediate discomfort of the protective gloves.

SUMMARY OF THE INVENTION

It is accordingly an object of the invention to provide for the skater a hand and wrist protective device that will enable the wearer to have free use of the thumb and fingers. It is another object that the device prevent hyperextension of the wrist joint and abrasion injury to the palm. It is yet another object that the device not enclose the hand so that air can circulate and perspiration evaporate from hand.

It is another object that the device be readily adjustable to hands and wrists of varying sizes. It is yet another object that the device, once adjusted, be readily strapped in place or removed using the other hand wearing the device.

These and other objects, features and advantages of the invention will become more apparent when the detailed description is considered in conjunction with the drawings, in which like reference characters are applied to like elements in the various figures.

BRIEF DESCRIPTION OF THE DRAWINGS

FIG. 1 is a side elevation view of the wrist protector in use.

FIG. 2 is a front elevation view of the wrist protector in use.

FIG. 3 is a sectional view taken through line 1—1 of FIG. 1.

FIG. 4 is a sectional view taken through line 2—2 of FIG. 2.

FIG. 5 is a sectional view of another embodiment of the invention taken through line A—A of FIG. 1.

FIG. 6 is a perspective view of the rigid plates of the invention.

DETAILED DESCRIPTION OF PREFERRED EMBODIMENTS

Referring now first to FIGS. 1–4 and 6.

Two thin, rigid formed plates of aluminum or hard, abrasion resistant plastic comprise a palm piece 2 and a dorsal piece 9. The palm piece 2 includes a wide palm portion 4 with a concave inner surface 12 to fit against the palm 22 of the hand, and a narrower medial wrist portion 3. The dorsal piece 9 includes a hand portion 10 with a convex inner surface 13 to restrain the hyperextension of the wrist joint and limit extension of the wrist 20 to an angle of not greater than 50° from the long axis of the forearm, and a dorsal wrist portion 11.

The wrist portions 3 and 11 are provided with longitudinal slots 17 and 18 respectively. Strap means 14 for joining the two pieces together securely on the wrist of the user pass through the slots and are bound tightly in place by hook and loop fasteners on the straps. As best seen in FIG. 3, a first strap assembly 24 is adjusted on one side of the wrist such that the two pieces 3, 9 will be substantially parallel when tightly fastened against the wrist. The strap assembly 24 includes a section 26 of hook strap passed through slot 17 and cemented together. Adhered to section 26 is a section 27 of loop strap which passes through slot 18 and is adjustably adhered again to strap 26 to provide the desired spacing on one side of the wrist. Once this adjustment is made, it can remain fixed while the protector is removed and replaced repeatedly.

Strap assembly 25 removably and adjustably secures the device to the second side of the wrist. Strap assembly 25 comprises a loop portion 28 cemented on piece 3. Sewn to portion 28 is elongate hook strap 29 which passes through slot 18 and is pulled tight and secured at its end 30 to the loop strap 28 cemented to piece 3. To remove the protector, the end 30 is pulled free and the two pieces moved apart on that side enough to pull the hand free without disturbing the adjustment of strap assembly 24.

This can be readily performed by one hand even if that hand wears a protector because the two pieces 3, 9 are only joined at the wrist. The anterior edges 32 and the lateral edges 31 of the palm and hand portions are unattached so that the thumb and fingers are free for use and air readily circulates about the hand for proper evaporation of perspiration.

Referring now to FIGS. 1, 2, 4–6, another embodiment of the invention is shown in which the palm piece 2 (FIG. 6) has two slots 17 and 23. A section 26 of hook strap passes through each slot 17 and 23 and is cemented together at its ends. Adhered to each section 26 is a strap 27 of loop material which passes through one or the other of the slots 28.

The ends 30 of the straps 27 is pulled taught so that the two pieces 3, 9 lie snug against the wrist and parallel to one another. The ends 30 are then folded back and secured against straps 26. Any extra strap 27 may be cut off on one side which serves as a fixed adjustment. The other side may retain the full length of its strap 27 and it may be secured against strap 26 with any surplus secured to a section of hook strap 33 cemented to piece 33.

Coating the inner surfaces of the pieces 3, 9 may be a resilient foam 34 with a moisture absorbing surface layer 35 for improved user comfort.

The wrist portions should have a length of at least 5 cm. and the hook and loop strap means should have a width of at least 3.8 cm. for effectively securing the protector to the wrist.

The above disclosed invention has a number of particular features which should preferably be employed in combination although each is useful separately without departure from the scope of the invention. While I have shown and described the preferred embodiments of my invention, it will be understood that the invention may be embodied otherwise than as herein specifically illustrated or described, and that certain changes in the form and arrangement of parts and the specific manner of practicing the invention may be made within the underlying idea or principles of the invention.

What is claimed:

1. A device for protecting the hand and wrist of a wearer, the device comprising:
   (A) a rigid palm piece having a palm portion with a width approximating the width of the palm of the wearer and a length extending only to below the fingers and thumb to thereby leave the thumb and fingers free for manipulation, a broad outer surface and a broad inner surface for application to the palm of the wearer, the inner surface being substantially concave;
   (B) an elongate medial wrist portion rigidly extending from the palm portion of the palm piece, having a width less than that of the palm portion, a length greater than 5 cm. and two long sides;
   (C) a rigid dorsal piece having a hand portion with a broad outer surface and a broad inner surface for application to the dorsum of the hand, the inner surface being substantially convex;
   (D) an elongate dorsal wrist portion rigidly extending from the hand portion of the dorsal piece, having a width less than that of the hand portion, a length of at least 5 cm. and two long sides; and
   (E) adjustable strap means having a width of at least 3.8 cm., the strap means for adjustably connecting a first long side of the dorsal wrist portion to a first long side of the medial wrist portion and also for separately adjustably connecting a second long side of the dorsal wrist portion to a second long side of the medial wrist portion to hold the device securely in position such that the palm and dorsal pieces will lie substantially parallel to one another and so that the strap means may release the two second long sides for removal of the device without disturbing the connection of the two first long sides, the hand being unencircled by the device.

2. The device according to claim 1, in which the inner surfaces of the palm piece and the dorsal piece are provided with resilient padding.

3. The device according to claim 2, further comprising hook and loop fastening means connected to the strap means for removably connecting the palm piece and the dorsal piece.

4. The device according to claim 1, adapted to limit extension of the wrist joint to an angle of not greater than 50° from the long axis of the forearm of said wearer.

5. The device according to claim 2, in which the palm piece is provided with a low friction, abrasion resistant outer surface.

6. The device according to claim 5, in which the palm piece and the dorsal piece are provided with moisture absorbing inner surfaces.

7. A device for protecting the hand and wrist of a wearer, the device comprising:
   (A) a rigid palm piece having a palm portion with a width approximating the width of the palm of the wearer and a length extending only to below the fingers and thumb to thereby leave the thumb and fingers free for manipulation, a broad outer surface and a broad inner surface for application to the palm of the wearer, the inner surface being substantially concave;
   (B) an elongate medial wrist portion rigidly extending from the palm portion of the palm piece, having a width less than that of the palm portion, a length greater than 5 cm. and two long sides;
   (C) a rigid dorsal piece having a hand portion with a broad outer surface and a broad inner surface for application to the dorsum of the hand, the inner surface being substantially convex;
   (D) an elongate dorsal wrist portion rigidly extending from the hand portion of the dorsal piece, having a width less than that of the hand portion, a length of at least 5 cm. and two long sides;
   (E) adjustable strap means for adjustably connecting a first long side of the dorsal wrist portion to a first long side of the medial wrist portion and also for separately adjustably connecting a second long side of the dorsal wrist portion to a second long side of the medial wrist portion to hold the device securely in position such that the palm and dorsal pieces will lie substantially parallel to one another and so that the strap means may release the two second long sides for removal of the device without disturbing the connection of the two first long sides; and
   (F) the palm portion and the hand portion being connected together only through the medial wrist portion and the dorsal wrist portion, and having anterior and lateral edges that are free of attachments, the hand being unencircled by the device.

8. The device according to claim 7, in which the inner surfaces of the palm piece and the dorsal piece are provided with resilient padding.

9. The device according to claim 8, further comprising hook and loop fastening means connected to the strap means for removably connecting the palm piece and the dorsal piece.

10. The device according to claim 7, adapted to limit extension of the wrist joint to an angle of not greater than 50° from the long axis of the forearm of said wearer.

11. The device according to claim 8, in which the palm piece is provided with a low friction, abrasion resistant outer surface.

12. The device according to claim 11, in which the palm piece and the dorsal piece are provided with moisture absorbing inner surfaces.

13. The device according to claim 12, in which the wrist portions are provided with elongate slots to receive the strap means.

* * * * *